United States Patent [19]

Ishihara et al.

[11] Patent Number: 4,973,740
[45] Date of Patent: Nov. 27, 1990

[54] PROCESS FOR PRODUCING TRICYCLODECANECARBOXYLIC ACID ESTERS

[75] Inventors: Masami Ishihara; Takeshi Morokuma, both of Okayama, Japan

[73] Assignees: Mitsubishi Gas Chemical Co., Inc.; Kao Corporation, both of Tokyo, Japan

[21] Appl. No.: 414,214

[22] Filed: Sep. 28, 1989

[30] Foreign Application Priority Data

Oct. 7, 1988 [JP] Japan ................................. 63-252020

[51] Int. Cl.$^5$ ...................... C07C 67/36; C07C 67/38; C07C 69/753
[52] U.S. Cl. .................................... 560/114; 560/117; 562/499; 562/848; 562/849; 562/851; 562/852
[58] Field of Search .......................................... 560/114

[56] References Cited

U.S. PATENT DOCUMENTS

| | | | |
|---|---|---|---|
| 2,448,368 | 8/1948 | Gresham et al. | 560/114 |
| 2,874,186 | 2/1959 | Friedman | 560/114 |
| 3,014,062 | 12/1961 | Moller et al. | 560/114 |
| 3,354,198 | 11/1967 | Friedman | 560/114 |
| 3,674,831 | 7/1972 | Rennick | 560/114 |
| 3,790,607 | 2/1974 | Lichstein | 560/114 |
| 4,138,580 | 2/1979 | Umemura et al. | 560/114 |
| 4,374,052 | 2/1983 | Fujikura et al. | 252/522 R |
| 4,411,828 | 10/1983 | Fujikura et al. | 252/522 R |
| 4,602,107 | 7/1986 | Fukikura et al. | 562/499 |
| 4,894,188 | 1/1990 | Takahishi et al. | 560/114 |

FOREIGN PATENT DOCUMENTS 743212  1/1956  United Kingdom ................ 560/114

OTHER PUBLICATIONS

Friedman et al., "J. Org. Chem.", vol. 27 (1962), pp. 481–486.

*Primary Examiner*—J. E. Evans
*Attorney, Agent, or Firm*—Browdy and Neimark

[57] ABSTRACT

A process for producing a tricyclodecanecarboxylic acid ester by reacting dihydrodicyclopentadiene with CO and an alcohol in the presence of anhydrous HF is disclosed. The reaction is performed in a solvent at a temperature of from −20° to 60° C. under a CO partial pressure of from 5 to 50 atm. The alcohol is used in an amount of 0.7 to 5 moles per mole of the dihydrodicyclopentadiene. The anhydrous HF is used in an amount of at least 5 moles per mole of the dihydrodicyclopentadiene. The product tricyclodecanecarboxylic acid ester is useful as a flavor.

8 Claims, No Drawings

PROCESS FOR PRODUCING TRICYCLODECANECARBOXYLIC ACID ESTERS

BACKGROUND OF THE INVENTION:

The present invention relates to a process for producing tricyclodecanecarboxylic acid esters useful as excellent flavors.

A known method for producing carboxylic acid esters from monoolefins consists of carbonylating the olefins with CO in strong acids by Koch reaction and esterifying the resulting carboxylic acids in acid catalysts. In order to produce esters of tricyclodecanecarboxylic acid (hereinafter abbreviated as TCDC), dicyclopentadiene (hereinafter abbreviated as DCPD) is hydrogenated and the resulting dihydrodicyclopentadiene (hereinafter abbreviated as DHDCPD) is reacted with CO and $H_2O$ in strong acids such as sulfuric acid to produce TCDC, which is then esterified. A problem with this method is that cycloolefins are so much susceptible to polymerization in the carbonylation reaction that TCDC cannot be obtained in high yield. With a view to avoiding this problem, U.S. Pat. No. 4,602,107 proposed a process for producing TCDC by bringing an inorganic strong acidic catalyst into contact with tricyclo[5.2.1.0$^{2.6}$]dec-8-yl formate that was obtained by reaction between DCPD and formic acid. The resulting carboxylic acid is esterified by reacting it with a dialkyl sulfate in contact with an aqueous alkaline solution (see U.S. Pat. Nos. 4,374,052 and 4,411,828).

The synthesis of TCDC by the method described in U.S. Pat. No. 4,602,107 proceeds by the following route of reaction:

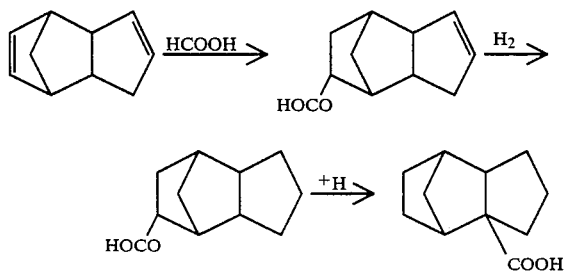

TCDC synthesis in a strong acid by this route of reaction involves rearrangement of the formate ester, which contributes to avoidance of the problem of susceptibility of olefins to polymerization in a strong acid, thereby improving the yield of TCDC that can be obtained. This approach, however, suffers the disadvantage of using a large volume of a strong acid such as sulfuric acid or anhydrous hydrofluoric acid. For example, in order to attain a high yield of TCDC, the strong acid must be used in an amount of at least 5 moles per mole of the reaction product. When sulfuric acid is used as the strong acid, it must be diluted with a large volume of water to liberate and recover TCDC from the reaction solution but this makes it impossible to put the sulfuric acid to another use. On the other hand, anhydrous hydrofluoric acid can be put to another use irrespective of its amount since it can be separated by distillation from the reaction product by making use of its highly volatile nature (b.p. 20° C.).

Noting this fact, the present inventors reviewed the possibility of synthesizing TCDC using anhydrous hydrofluoric acid as a catalyst. As a result, it was found that part of the formate ester used as a starting material decomposed without being converted to TCDC and that the formation of formic acid and high-boiling point materials was unavoidable. The resulting free formic acid formed a mixture with HF, leading to the formation of $HF-H_2O$ and generation of CO by decomposition of the formic acid. This causes not only the loss of the catalyst HF but also various process troubles such as increased corrosion of the reactor and difficulty in the operation of catalyst regeneration. All these phenomena combine to reduce the process economy of TCDC synthesis significantly.

TCDC must be esterified before it can be used as a flavor. Tertiary carboxylic acids are generally difficult to esterify and the effect of steric hindrance is particularly great in the case of TCDC. In this method described in U.S. Pat. Nos. 4,374,052 and 4,411,828, diethyl sulfate is used as an esterifying agent but it decomposes in the presence of water that forms as a result of reaction. In order to increase the yield of the final product, an aqueous alkaline solution must be added in many divided portions, which is quite a cumbersome operation to perform. Further, the use of expensive diethyl sulfate reduces the economy of the overall process.

SUMMARY OF THE INVENTION:

The present inventors conducted intensive studies in order to develop a process for producing TCDC esters without suffering from the aforementioned problems of the prior art. As a result, they found that when the starting DHDCPD was reacted with CO and an alcohol in anhydrous hydrofluoric acid, carbonylation and esterification reactions took place simultaneously, with a desired carboxylic acid ester being produced in high yield. The present invention has been accomplished on the basis of this finding.

The present invention relates to a process for producing a tricyclodecanecarboxylic acid ester by reacting dihydrodicyclopentadiene with CO and an alcohol in the presence of anhydrous hydrofluoric acid.

DETAILED DESCRIPTION OF THE INVENTION:

The starting material used in the present invention is DHDCPD which is obtained by hydrogenating DCPD. The alcohol used for esterification is a lower monohydric alcohol such as methanol or ethanol. The alcohol is used in an amount of 0.7-5 moles, preferably 1-3 moles, per mole of the starting monoolefin. If the molar ratio of alcohol to monoolefin is less than 0.7, the alcohol is insufficient to produce an ester in satisfactory yield. If the alcohol to monoolefin molar ratio is greater than 5, the excess alcohol reduces the rate of carbonylation reaction and hence, the yield of ester production.

In the process of the present invention, substantially; anhydrous hydrofluoric acid is used as a catalyst. The hydrofluoric acid is used in an amount of at least 5 moles, preferably 10-25 moles, per mole of the starting DHDCPD. If the molar ratio of HF is less than 5, the yield of ester production will decrease. If the molar ratio of HF is more than 25, the improvement in ester yield is small whereas the cost of HF separation will increase.

The reaction temperature to be employed in the process of the present invention is within the range of from −20° to 60° C. Below −20° C., the reaction rate is so low as to cause reduction in the yield of ester production. Above 60° C., a side reaction will occur to cause undesired polymerization of the reaction product.

In the process of the present invention, the reaction proceeds in a pressurized CO atmosphere. The CO used as a reactant may contain an inert gas such as $N_2$ or $CH_4$. The CO partial pressure is within the range of 5–50 atmosphere, preferably 10–30 atmosphere. If the CO partial pressure is too low, carbonylation reaction will not proceed sufficiently to insure high yield. If the CO partial pressure is too high, the reaction may proceed but a high-pressure apparatus is necessary and an increased power is required to compress CO.

The pressure decreases as the reaction proceeds, so it is desirable to supply additional CO continuously in the present invention. The process of the present invention is preferably performed on a semi-continuous or continuous basis.

By using a solvent that highly dissolves the starting DHDCPD but which is inert to HF in the present invention, the undesired polymerization reaction is suppressed and the yield of ester is improved. Illustrative solvents that can be used for this purpose include saturated aliphatic hydrocarbons such as pentane and hexane, and halogenated hydrocarbons such as methane chloride and ethane chloride.

The reaction product is separated by distillation which comprises first distilling off HF and then fractionating the high-boiling point materials to obtain the product TCDC ester.

The reaction involved in the process of the present invention proceeds by the following route:

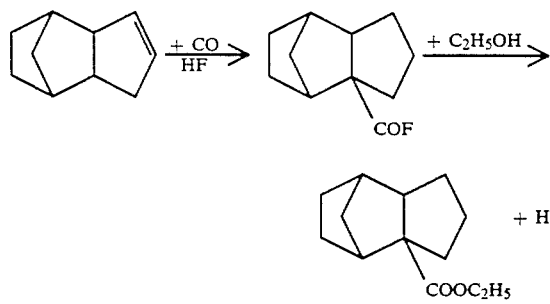

an acid fluoride is first generated, which then reacts with an alcohol to produce an ester in one step. Since neither the carboxylic acid nor $H_2O$ participates in this route of reaction, a very advantageous process can be realized as described in the next paragraph. A strong proton catalyst such as anhydrous hydrofluoric acid is usually required in carbonylating olefins but at the same time, the polymerization of olefin which occurs as a side reaction is promoted by the proton acid. In the present invention, an alcohol is allowed to be present in the reaction system and the acidity of anhydrous hydrofluoric acid is reasonably attenuated, thereby reducing the rate of polymerization and improving the yield of carbonylation reaction. The alcohol in the reaction system has the added advantage of suppressing the occurrence of unwanted polymerization by promoting the dissolution and dispersion of the starting DHDCPD in HF.

In accordance with the process of the present invention, a TCDC ester can be readily produced from DHDCPD which is obtained by hydrogenating inexpensive DCPD. Neither carboxylic acid nor $H_2O$ takes part in the reaction involved in the process of the present invention, so sulfuric acid which is normally used in large amounts in esterification reaction and a special chemical such as diethyl sulfate can be entirely dispensed with, and the equipment will not be seriously corroded by HF. In addition, HF used as a catalyst in the present invention can be readily separated and recovered by distillation for further use. As a result, no effluents that need be treated by anti-pollution measures will be generated, contributing to efficient utilization of resources.

The following examples are provided for the purpose of further illustrating the present invention but are in no way to be taken as limiting.

EXAMPLES 1–4

A stainless steel autoclave (200 ml) equipped with a stirrer was charged with anhydrous HF as a catalyst. Under thorough stirring and with warm or cold water being circulated through the jacket to maintain a predetermined reaction temperature, the atmosphere in the autoclave was pressurized with CO gas to a predetermined level while a liquid mixture of the reactants, DHDCPD and an alcohol (and a solvent as required) was continuously fed into the autoclave by means of metering pump. As the reaction proceeded, the pressure in the autoclave would decrease, so an additional amount of CO gas was supplied in order to maintain the predetermined pressure. After completion of its supply, the feed solution was allowed to stay in the autoclave for ca. 30 minutes and a sample was taken into ice water for analysis by gas chromatography. The operating conditions employed in the respective examples and the yields of the esters recovered are shown in Table 1 below.

TABLE 1

|  | Example | | | |
| --- | --- | --- | --- | --- |
|  | 1 | 2 | 3 | 4 |
| Amount of feeds (mol) | | | | |
| DHDCPD | 0.78 | 1.07 | 1.17 | 1.0 |
| ethanol | 1.0 | 1.0 | 1.0 | 1.0 |
| pentane (solvent) | — | — | — | 2.0 |
| HF/DHDCPD molar ratio | 15.4 | 20.2 | 23.0 | 20.0 |
| Reaction temperature (°C.) | 10 | 5 | 0 | 5 |
| CO partial pressure (kg/cm$^2$G) | 18.0 | 18.5 | 18.0 | 18.0 |
| Yield of ester | 68.4 | 71.0 | 68.8 | 72.5 |

What is claimed is:

1. A process for producing a tricyclodecanecarboxylic acid ester by reacting dihydrodicyclopentadiene with CO and an alcohol in the presence of anhydrous HF.

2. A process according to claim 1 wherein said alcohol is a lower monohydric alcohol.

3. A process according to claim 2 wherein said lower monohydric alcohol is methanol and/or ethanol.

4. A process according to claim 1 wherein said alcohol is used in an amount of 0.7–5 moles per mole of the dihydrodicyclopentadiene.

5. A process according to claim 1 wherein said anhydrous HF is used in an amount of at least 5 moles per mole of the dihydrodicyclopentadiene.

6. A process according to claim 1 wherein the reaction is performed at a temperature in the range of from −20° to 60° C.

7. A process according to claim 1 wherein the reaction is performed at a CO partial pressure of 5–50 atmospheres.

8. A process according to claim 1 wherein the reaction is performed in a solvent selected from the group consisting of saturated aliphatic hydrocarbons and halogenated hydrocarbons.

* * * * *